(12) United States Patent
Claypool et al.

(10) Patent No.: US 8,747,410 B2
(45) Date of Patent: Jun. 10, 2014

(54) PATELLAR RESECTION INSTRUMENT WITH VARIABLE DEPTH GUIDE

(75) Inventors: Jody L. Claypool, Columbia City, IN (US); Steven Stump, Goshen, IN (US)

(73) Assignee: Zimmer, Inc., Warsaw, IN (US)

( * ) Notice: Subject to any disclaimer, the term of this patent is extended or adjusted under 35 U.S.C. 154(b) by 181 days.

(21) Appl. No.: 12/912,262

(22) Filed: Oct. 26, 2010

(65) Prior Publication Data
US 2012/0101505 A1 Apr. 26, 2012

(51) Int. Cl.
*A61B 17/56* (2006.01)

(52) U.S. Cl.
USPC .............................. 606/88; 606/99; 606/102

(58) Field of Classification Search
USPC ........... 606/88, 79, 87, 96, 99, 102, 86 R, 90, 606/105; 623/20.18–20.2; 403/109.2, 403/109.3, 109.6, 109.7, 146, 348, 349, 403/378, 327, 330, 322.4, 104, 106, 107; 285/302, 303, 376, 401, 402
See application file for complete search history.

(56) References Cited

U.S. PATENT DOCUMENTS

| | | | |
|---|---|---|---|
| 1,170,334 A | | 2/1916 | Riggs |
| 2,411,944 A | * | 12/1946 | Stone ............................. 606/116 |
| 2,564,118 A | | 8/1951 | Mahorner |
| 2,779,224 A | * | 1/1957 | Coggburn ....................... 81/3.44 |
| 3,230,595 A | * | 1/1966 | Kedem .......................... 403/376 |
| 3,470,872 A | * | 10/1969 | Grieshaber ................... 600/217 |
| 3,583,403 A | * | 6/1971 | Pohl et al. ..................... 606/132 |
| 3,870,268 A | * | 3/1975 | Larkin ......................... 248/354.1 |
| 3,933,011 A | * | 1/1976 | DiGilio et al. ................. 63/29.1 |
| 4,034,746 A | * | 7/1977 | Williams ....................... 600/217 |
| 4,101,157 A | * | 7/1978 | Richey ......................... 294/86.21 |
| 4,112,951 A | * | 9/1978 | Hulka et al. ................... 128/831 |
| 4,305,180 A | * | 12/1981 | Schwartz ....................... 439/296 |
| 4,312,337 A | * | 1/1982 | Donohue ......................... 606/80 |
| 4,457,307 A | | 7/1984 | Stillwell |
| 4,524,766 A | | 6/1985 | Petersen |

(Continued)

FOREIGN PATENT DOCUMENTS

| | | |
|---|---|---|
| EP | 0791335 A1 | 8/1997 |
| FR | 2732210 A1 | 10/1996 |
| JP | 08-098842 A | 4/1996 |
| WO | WO98/32384 A1 | 7/1998 |

OTHER PUBLICATIONS

Zimmer Natural-Knee II Patello-femoral Joint System Surgical Technique, 2004 Zimmer, Inc.

(Continued)

*Primary Examiner* — Michael T Schaper
*Assistant Examiner* — Tracy Kamikawa
(74) *Attorney, Agent, or Firm* — Schwegman Lundberg & Woessner, P.A.

(57) ABSTRACT

A patellar resection instrument has an integral depth adjustment assembly that is easily, intuitively, and intra-operatively adjustable between a plurality of discrete positions. Each position corresponds to a particular, known depth of resection, and this depth may optionally be inscribed on the depth adjustment knob for easy visual selection and/or confirmation of the resection depth. The depth adjustment assembly provides positive tactile feedback as the stylus is moved between positions. The unique configuration of the depth adjustment assembly maintains the resection depth stylus in a chosen position throughout the patellar resection procedure, even if the procedure causes vibration or other forces to be transmitted to the patellar resection instrument.

12 Claims, 7 Drawing Sheets

(56) References Cited

U.S. PATENT DOCUMENTS

| | | | | |
|---|---|---|---|---|
| 4,565,192 | A | 1/1986 | Shapiro | |
| 4,566,448 | A | 1/1986 | Rohr, Jr. | |
| 4,574,794 | A | 3/1986 | Cooke | |
| 4,633,862 | A * | 1/1987 | Petersen | 606/88 |
| 4,718,413 | A | 1/1988 | Johnson | |
| 4,721,104 | A | 1/1988 | Kaufman | |
| 4,722,330 | A | 2/1988 | Russell et al. | |
| 4,759,350 | A | 7/1988 | Dunn | |
| 4,841,975 | A | 6/1989 | Woolson | |
| 4,892,093 | A | 1/1990 | Zarnowski et al. | |
| 4,896,661 | A * | 1/1990 | Bogert et al. | 606/86 R |
| 4,926,847 | A | 5/1990 | Luckman | |
| 4,926,849 | A | 5/1990 | Downey | |
| 4,935,023 | A | 6/1990 | Whiteside et al. | |
| 4,943,181 | A * | 7/1990 | Murphy | 403/324 |
| 5,002,545 | A | 3/1991 | Whiteside et al. | |
| 5,002,547 | A | 3/1991 | Poggie et al. | |
| 5,007,912 | A | 4/1991 | Albrektsson | |
| 5,021,055 | A * | 6/1991 | Burkinshaw et al. | 606/82 |
| 5,035,699 | A | 7/1991 | Coates | |
| 5,047,032 | A | 9/1991 | Jellicoe | |
| 5,053,039 | A | 10/1991 | Hofmann et al. | |
| 5,062,846 | A * | 11/1991 | Oh et al. | 606/158 |
| 5,080,675 | A | 1/1992 | Lawes et al. | |
| 5,098,436 | A | 3/1992 | Ferrante | |
| 5,100,409 | A | 3/1992 | Coates | |
| 5,108,401 | A * | 4/1992 | Insall et al. | 606/79 |
| 5,122,144 | A | 6/1992 | Bert et al. | |
| 5,129,907 | A | 7/1992 | Heldreth | |
| 5,129,908 | A * | 7/1992 | Petersen | 606/88 |
| 5,147,365 | A * | 9/1992 | Whitlock et al. | 606/88 |
| 5,176,684 | A | 1/1993 | Ferrante | |
| 5,180,384 | A | 1/1993 | Mikhail | |
| 5,186,197 | A * | 2/1993 | Lavine | 135/25.4 |
| 5,207,680 | A | 5/1993 | Dietz | |
| 5,219,362 | A | 6/1993 | Tuke et al. | |
| 5,222,955 | A | 6/1993 | Mikhail | |
| 5,234,433 | A | 8/1993 | Bert et al. | |
| 5,284,482 | A | 2/1994 | Mikhail | |
| 5,306,285 | A | 4/1994 | Miller et al. | |
| 5,330,533 | A | 7/1994 | Walker | |
| 5,342,366 | A | 8/1994 | Whiteside et al. | |
| 5,344,423 | A | 9/1994 | Dietz | |
| 5,364,401 | A | 11/1994 | Ferrante et al. | |
| 5,415,663 | A | 5/1995 | Luckman et al. | |
| 5,417,694 | A | 5/1995 | Marik et al. | |
| 5,417,695 | A | 5/1995 | Axelson | |
| 5,454,816 | A | 10/1995 | Ashby | |
| 5,474,559 | A | 12/1995 | Bertin | |
| 5,486,178 | A | 1/1996 | Hodge | |
| 5,486,180 | A | 1/1996 | Dietz | |
| 5,514,139 | A | 5/1996 | Goldstein | |
| 5,520,692 | A | 5/1996 | Ferrante | |
| 5,520,695 | A | 5/1996 | Luckman | |
| 5,536,271 | A | 7/1996 | Daly et al. | |
| 5,540,696 | A | 7/1996 | Booth | |
| 5,542,947 | A * | 8/1996 | Treacy | 606/88 |
| 5,569,261 | A | 10/1996 | Marik et al. | |
| 5,593,411 | A | 1/1997 | Stalcup | |
| 5,597,379 | A | 1/1997 | Haines | |
| 5,601,563 | A | 2/1997 | Burke et al. | |
| 5,609,639 | A | 3/1997 | Walker | |
| 5,643,272 | A | 7/1997 | Haines | |
| 5,658,291 | A | 8/1997 | Techiera | |
| 5,658,292 | A | 8/1997 | Axelson | |
| 5,658,293 | A | 8/1997 | Vanlaningham | |
| 5,662,656 | A | 9/1997 | White | |
| 5,667,512 | A | 9/1997 | Johnson | |
| 5,674,244 | A * | 10/1997 | Mathys | 606/208 |
| 5,676,668 | A | 10/1997 | McCue et al. | |
| 5,683,397 | A | 11/1997 | Vendrely et al. | |
| 5,688,280 | A | 11/1997 | Booth | |
| 5,688,281 | A | 11/1997 | Cripe et al. | |
| 5,693,048 | A | 12/1997 | Stalcup | |
| 5,702,466 | A | 12/1997 | Pappas et al. | |
| 5,716,360 | A | 2/1998 | Baldwin et al. | |
| 5,716,362 | A * | 2/1998 | Treacy | 606/87 |
| 5,720,752 | A | 2/1998 | Elliott et al. | |
| 5,743,915 | A | 4/1998 | Bertin | |
| 5,749,876 | A | 5/1998 | Duvillier et al. | |
| 5,755,803 | A | 5/1998 | Haines | |
| 5,769,855 | A | 6/1998 | Bertin | |
| 5,782,920 | A | 7/1998 | Colleran | |
| 5,810,827 | A | 9/1998 | Haines | |
| 5,810,831 | A | 9/1998 | D'Antonio | |
| 5,830,216 | A | 11/1998 | Insall | |
| 5,853,415 | A | 12/1998 | Bertin | |
| 5,860,981 | A | 1/1999 | Bertin | |
| 5,879,354 | A | 3/1999 | Haines | |
| 5,885,298 | A | 3/1999 | Herrington et al. | |
| 5,908,424 | A | 6/1999 | Bertin | |
| 5,910,143 | A | 6/1999 | Cripe et al. | |
| 5,911,723 | A | 6/1999 | Ashby et al. | |
| 5,914,884 | A | 6/1999 | Gur Ali et al. | |
| 5,931,777 | A * | 8/1999 | Sava | 600/213 |
| 5,941,884 | A * | 8/1999 | Corvelli et al. | 606/88 |
| 5,980,170 | A | 11/1999 | Salyer | |
| 6,010,509 | A * | 1/2000 | Delgado et al. | 606/88 |
| 6,013,081 | A | 1/2000 | Burkinshaw et al. | |
| 6,056,754 | A | 5/2000 | Haines et al. | |
| 6,059,831 | A | 5/2000 | Braslow et al. | |
| 6,102,954 | A | 8/2000 | Albrektsson et al. | |
| 6,159,214 | A * | 12/2000 | Michelson | 606/80 |
| 6,159,217 | A * | 12/2000 | Robie et al. | 606/88 |
| 6,159,246 | A | 12/2000 | Mendes et al. | |
| 6,174,314 | B1 | 1/2001 | Waddell | |
| 6,193,756 | B1 * | 2/2001 | Studer et al. | 623/17.15 |
| 6,197,064 | B1 | 3/2001 | Haines | |
| 6,221,089 | B1 * | 4/2001 | Mawhirt | 606/181 |
| D450,120 | S * | 11/2001 | Adler et al. | D24/143 |
| 6,575,980 | B1 | 6/2003 | Robie et al. | |
| 6,602,258 | B1 * | 8/2003 | Katz | 606/80 |
| 6,695,848 | B2 | 2/2004 | Haines | |
| 6,702,824 | B2 * | 3/2004 | Maroney et al. | 606/99 |
| 6,740,092 | B2 | 5/2004 | Lombardo et al. | |
| 6,770,077 | B2 | 8/2004 | Van Zile et al. | |
| 6,852,119 | B1 * | 2/2005 | Abulhaj et al. | 606/182 |
| 6,959,629 | B2 * | 11/2005 | Hsien | 81/177.2 |
| 7,048,741 | B2 | 5/2006 | Swanson | |
| 7,052,504 | B2 * | 5/2006 | Hughett | 606/142 |
| 7,156,853 | B2 * | 1/2007 | Muratsu | 606/102 |
| 7,156,874 | B2 * | 1/2007 | Paponneau et al. | 623/17.11 |
| 7,344,540 | B2 | 3/2008 | Smucker et al. | |
| 7,351,244 | B2 * | 4/2008 | Hamada | 606/102 |
| 7,497,149 | B2 * | 3/2009 | Lin | 81/62 |
| D592,747 | S * | 5/2009 | Weiler et al. | D24/143 |
| 7,632,279 | B2 * | 12/2009 | Bastian | 606/88 |
| 7,635,370 | B2 * | 12/2009 | Michelson | 606/96 |
| 7,799,086 | B2 * | 9/2010 | Justin et al. | 623/20.32 |
| 7,806,899 | B2 * | 10/2010 | Hogg et al. | 606/88 |
| 8,118,811 | B2 * | 2/2012 | Coon et al. | 606/88 |
| 8,147,497 | B2 * | 4/2012 | Sherry et al. | 606/88 |
| 8,162,949 | B2 * | 4/2012 | Duggineni et al. | 606/88 |
| 8,182,488 | B2 * | 5/2012 | Oliver | 606/87 |
| 8,216,244 | B2 * | 7/2012 | Green et al. | 606/102 |
| D666,720 | S * | 9/2012 | Kecman et al. | D24/140 |
| D666,721 | S * | 9/2012 | Wright et al. | D24/140 |
| 8,268,004 | B2 * | 9/2012 | Castleman et al. | 623/17.16 |
| 8,287,547 | B2 * | 10/2012 | Martin et al. | 606/96 |
| 2002/0133157 | A1 * | 9/2002 | Sterett et al. | 606/69 |
| 2003/0100907 | A1 | 5/2003 | Rosa et al. | |
| 2003/0212403 | A1 | 11/2003 | Swanson | |
| 2004/0162561 | A1 | 8/2004 | Marchyn et al. | |
| 2005/0273115 | A1 * | 12/2005 | Coon et al. | 606/88 |
| 2006/0020288 | A1 * | 1/2006 | Leonard | 606/205 |
| 2006/0142777 | A1 * | 6/2006 | Bastian | 606/88 |
| 2007/0118141 | A1 * | 5/2007 | Marchyn et al. | 606/88 |
| 2007/0179524 | A1 * | 8/2007 | Weber et al. | 606/205 |
| 2007/0233142 | A1 * | 10/2007 | Oliver | 606/88 |
| 2008/0114366 | A1 * | 5/2008 | Smucker et al. | 606/88 |
| 2008/0306484 | A1 | 12/2008 | Coon et al. | |
| 2009/0043310 | A1 * | 2/2009 | Rasmussen | 606/88 |

(56) References Cited

U.S. PATENT DOCUMENTS

2009/0318927 A1* 12/2009 Martin et al. .................. 606/96
2010/0076441 A1 3/2010 May et al.
2012/0078261 A1* 3/2012 Kecman et al. ................ 606/88

OTHER PUBLICATIONS

Zimmer NexGen Trabecular Metal Primary Patella Surgical Technique, 2005 Zimmer, Inc.
European Office Action mailed Sep. 3, 2010 in European Application No. EP03743240.8.
European Search Report mailed Apr. 20, 2010 in European Patent Application No. EP03743240.8.
International Search Report from International Application No. PCT/US2003/05726 corresponding to U.S. Appl. No. 10/373,930.
Zimmer, Inc. Nexgen Complete Knee Solution, Intramedullary Instrumentation Surgical Technique for the NexGen Cruciate Retaining & Legacy Posterior Stabilized knee, 97-5973-102 Rev. 1, 1995, 1997, 1998.
Zimmer, Inc. Nexgen Complete Knee Solution, Multi-Reference 4-in-1 Femoral Instrumentation, Posterior Reference Surgical Technique, 97-5973-402 Rev. 1, 1998, 2000.
Zimmer, Inc. Nexgen Complete Knee Solution, Revision Instrumentation Surgical Technique for Legacy Knee Constrained Condylar Knee, 97-5994-202, 2001.
Zimmer, Inc. Nexgen Complete Knee Solution, Extramedullary/Intramedullary Tibial Resector Surgical Technique, 97-5997-02 Rev. 1, 2000, 2002.
Zimmer, Inc. Nexgen Complete Knee Solution, Primary/Revision Surgical Technique for NexGen Rotating Hinge Knee (RHK), 97-5880-02, 2002.
Zimmer, Inc. Nexgen Complete Knee Solution, Surgical Technique for the Legacy Knee LPS-Flex Fixed Bearing Knee, 97-5964-02 Rev. 1, 2000, 2002.
Zimmer, Inc. Nexgen Complete Knee Solution, Surgical Technique for the Legacy Posterior Stabilized Knees, 97-5996-02, 2002.
Zimmer, Inc. Nexgen Complete Knee Solution, Surgical Technique for Cruciate Retaining Knees and Revision Instrumentation Surgical Technique for Cruciate Retaining Augmentable Knees, 97-5970-202, 2002, 2005, 2008, 2011.
Zimmer, Inc. MIS Minimally Invasive Solution, The M/G Unicompartmental Knee Minimally Invasive Surgical Technique, 97-5791-02, 2002.
Zimmer, Inc. Revision Knee Arthroplasty Surgical Guidelines, 2nd Edition, 97-5224-03, 1999.

* cited by examiner

PATELLAR RESECTION INSTRUMENT WITH VARIABLE DEPTH GUIDE

BACKGROUND

1. Technical Field

The present disclosure relates to surgical instruments and, more particularly, to surgical instruments used in the resection of a patella during knee arthroplasty.

2. Description of the Related Art

Orthopedic prostheses are commonly utilized to repair or replace damaged bone and tissue in the human body. For example, a knee prosthesis may include a patellofemoral prosthesis designed to replace the natural patellofemoral groove, also called the femoral sulcus, formed in the distal portion of the femur. In total knee arthroplasty, for example, a femoral component designed to replace the entire distal portion of the natural femur includes an anterior flange which serves as a patellofemoral prosthesis. In some other surgical procedures, such as partial knee arthroplasty, a separate patellofemoral component can be implanted to replace the femoral sulcus.

A patellar prosthesis may also be used in knee arthroplasty procedures. The patella prosthesis replaces a portion of the natural patella, and is designed to articulate with the patellofemoral prosthesis. Alternatively, a surgeon may forego the use of a patellofemoral component and implant only the patellar prosthesis, which then articulates with the natural patellofemoral groove of the femur. In a typical implantation of a patellar prosthesis, the anterior portion of the natural patella is retained while the posterior, articulating portion of the patella is replaced with a prosthetic component. Replacing only the articulating surface of the patella preserves ligament connections between the natural patella and the surrounding anatomical structures. To make such a "partial" patellar replacement, the posterior portion of the patella is resected and the prosthetic patellar component is affixed to the resected surface.

To perform a resection of the posterior portion of the patella for receipt of a particular prosthesis, the depth of resection is controlled to remove a known amount of the natural bone stock of the anatomic patella. The chosen prosthesis replaces the removed bone stock to yield a desired prosthetic patellar articular surface.

SUMMARY

The present disclosure provides a patellar resection instrument with an integral depth adjustment assembly that is easily, intuitively, and intra-operatively adjustable between a plurality of discrete positions. Each position corresponds to a particular, known depth of resection, and this depth may optionally be inscribed on the depth adjustment knob for easy visual selection and/or confirmation of the resection depth. The depth adjustment assembly provides positive tactile feedback as the stylus is moved between positions. The unique configuration of the depth adjustment assembly maintains the resection depth stylus in a chosen position throughout the patellar resection procedure, even if the procedure causes vibration or other forces to be transmitted to the patellar resection instrument.

In one aspect thereof, the present invention provides a surgical instrument for use in resection of a patella, the instrument comprising: a cut guide defining a cut guide surface, the cut guide adapted to guide a cutting tool through at least a portion of the patella along the cut guide surface; and an integral depth adjustment assembly comprising: an adjustment body coupled to the cut guide; a stylus slidably coupled to the adjustment body, the stylus having a bone contacting surface movable between a plurality of discrete stylus positions, each position defining a predefined stylus distance between the cut guide surface and the bone contacting surface, whereby each stylus distance corresponds to a different resection depth of the patella when the patella is in contact with the stylus; and a biasing element biasing the stylus into one of the discrete positions when the biasing element is acted upon only by forces within the depth adjustment assembly.

In another aspect thereof, the present invention provides a surgical instrument for use in resection of a patella, the instrument comprising: an instrument body; means for fixing the patella to the instrument body; a cut guide having a cut guide surface; and resection depth selection means for selecting a predefined resection depth, the depth selection means integral with the instrument body, the depth selection means including a stylus having a bone contacting surface, the resection depth equal to a distance between the bone contacting surface and the cut guide surface.

In yet another aspect thereof, the present invention provides a method of resecting a patella with a surgical instrument including a cut guide and an integral depth adjustment assembly, the depth adjustment assembly including: an adjustment body coupled to the surgical instrument; a stylus slidably coupled to the adjustment body, the stylus defining a plurality of discrete positions with respect to the adjustment body, each position corresponding to a resection depth of the patella; and a biasing element biasing the stylus into each of the discrete positions, the biasing element urging the stylus into one of the discrete positions when the biasing element is acted upon only by forces within the depth adjustment assembly, the method comprising: adjusting the depth adjustment assembly into one of the discrete positions to define a resection depth of the patella; contacting the patella with the stylus; while maintaining the contact between the patella and the stylus and after the step of adjusting the depth adjustment assembly, coupling the cut guide of the surgical instrument onto the patella; and resecting the patella using the cut guide.

BRIEF DESCRIPTION OF THE DRAWINGS

The above-mentioned and other features and advantages of this invention, and the manner of obtaining them, will become more apparent and the invention itself will be better understood by reference to the following descriptions of an embodiment of the invention taken in conjunction with the accompanying drawings, wherein.

Corresponding reference characters indicate corresponding parts throughout the several views. The exemplification set out herein illustrates an exemplary embodiment of the invention, and such exemplification is not to be construed as limiting the scope of the invention in any matter.

DETAILED DESCRIPTION

Figure 1:
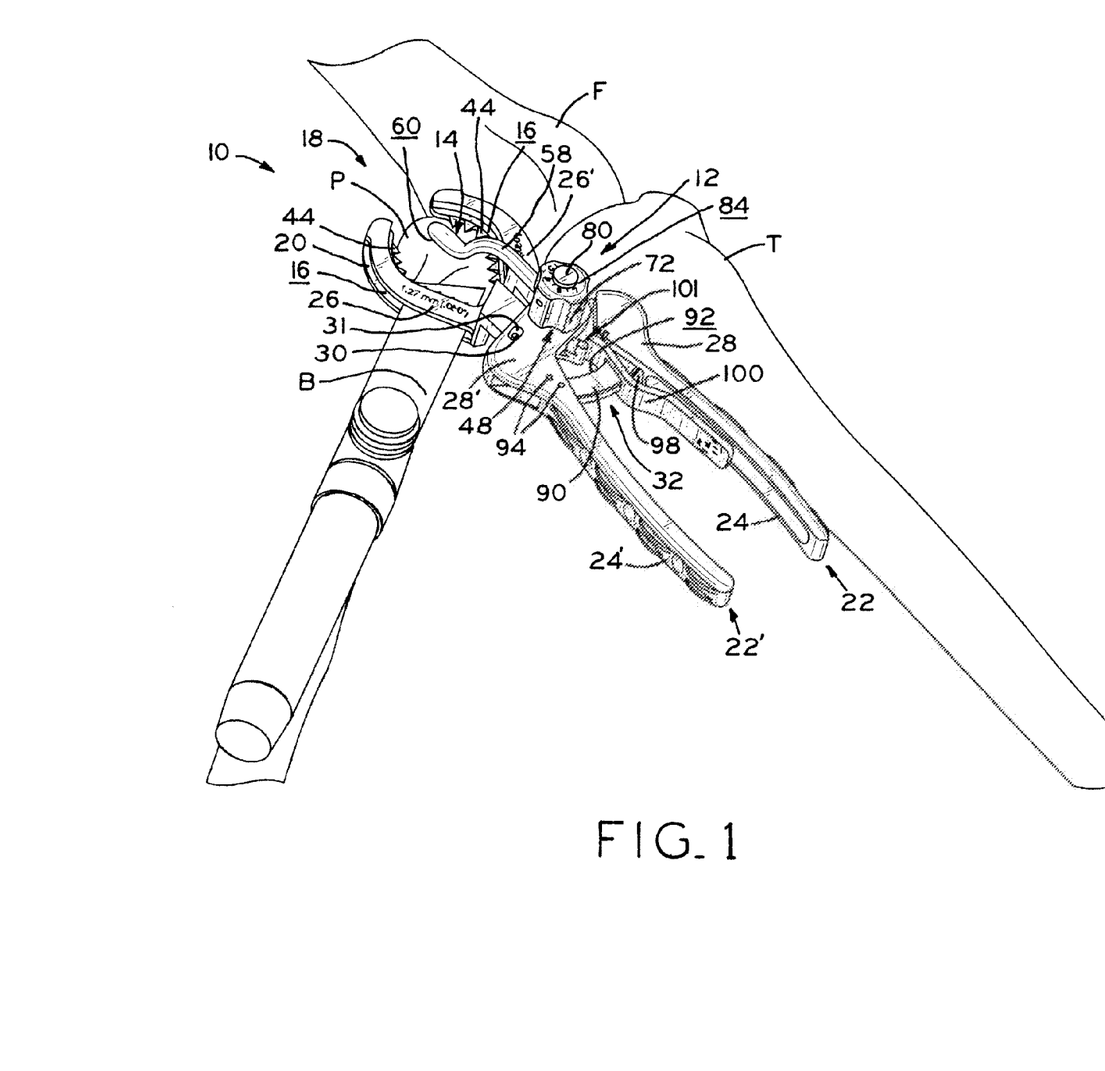
FIG. 1 is a perspective view with a patellar resection instrument in accordance with the present disclosure, illustrating the instrument in use.

Referring now to FIG. 1, patella resection instrument 10 includes a detent mechanism, such as depth adjustment assembly 12, operable to move resection depth stylus 14 between a plurality of discrete positions relative to cut guide surfaces 16. Each position corresponds to a known and enumerated resection depth D (FIG. 3) that will result when instrument 10 is used to resect patella P. In the exemplary embodiment shown and described herein, resection depth D is the largest distance between the cut guide surfaces (16), formed in clamping portion 18 of instrument 10, and bone contacting surface 60 of stylus 14 along a line substantially normal to surfaces 16, 60. Although depth adjustment assembly 12 is described below as including scalloped region 70 (FIGS. 3A-3C) operable to adjust the height of stylus 14, it is contemplated that other detent mechanisms may be used in accordance with the present disclosure, with a plurality of detents each defining a position of stylus 14, and therefore defining resection depth D.

Prior to resection of the patella, depth adjustment assembly 12 is manipulated to set resection depth D to a particular desired value or distance. Stylus 14 is brought into contact with patella P, which is then clamped within clamping portion 18 while maintaining the patella/stylus contact. With patella P secured in clamping portion 18, blade B (FIG. 1) or other cutting tool is passed through cut slots 20, 20' formed in clamp arms 26, 26' of clamping portion 18 to resect patella P. After the resection is complete, the resected surface of the remaining portion of patella P is substantially coplanar with the lower cut guide surfaces 16. For purposes of the following discussion, the "lower" cut guide surface 16 in each of clamp arms 26, 26' is the cut guide surface furthest from bone contacting surface 60 of stylus 14. Thus, the distance between bone contacting surface 60 of stylus 14 and lower cut guide surfaces 16 corresponds to resection depth D, i.e., the total depth of bone removed from patella P.

As described below, an exemplary embodiment of patella resection instrument 10 includes springs 30, 64, 106, which act upon various structures of patella resection instrument 10 to provide a biasing force. However, it is contemplated that any suitably biasing element may be used in lieu of any of springs 30, 64, 106. Alternative biasing elements include elastomeric materials and magnetic elements, for example.

Figure 4:
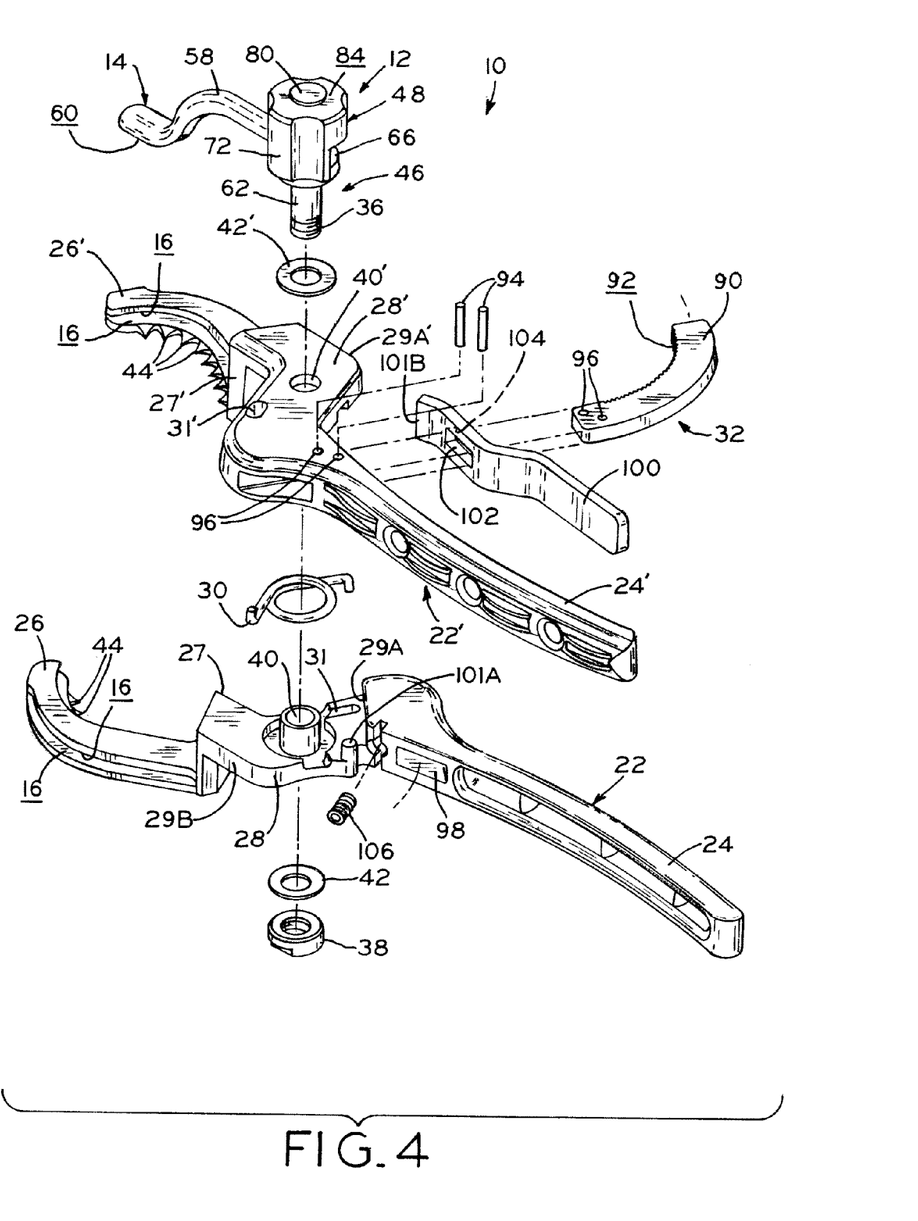
FIG. 4 is a perspective, exploded view of the patellar resection instrument shown in FIG. 1.

Referring to FIGS. 1 and 4, patella resection instrument 10 includes first and second instrument bodies 22, 22' each having handles 24, 24' and patellar clamp arms 26, 26'. Bodies 22, 22' are joined by pivots 28, 28' disposed between handles 24, 24' and clamp arms 26, 26', respectively. Torsion spring 30 spans pivots 28, 28' and acts on both of instrument bodies 22, 22' to bias handles 24, 24' and clamp arms 26, 26' away from one another and into an open configuration (solid lines of FIG. 2). As discussed below, ratchet mechanism 32 (FIGS. 2 and 4) operates to hold instrument 10 in a closed position (dashed lines of FIG. 2) against the biasing force of torsion spring 30.

Figure 2:
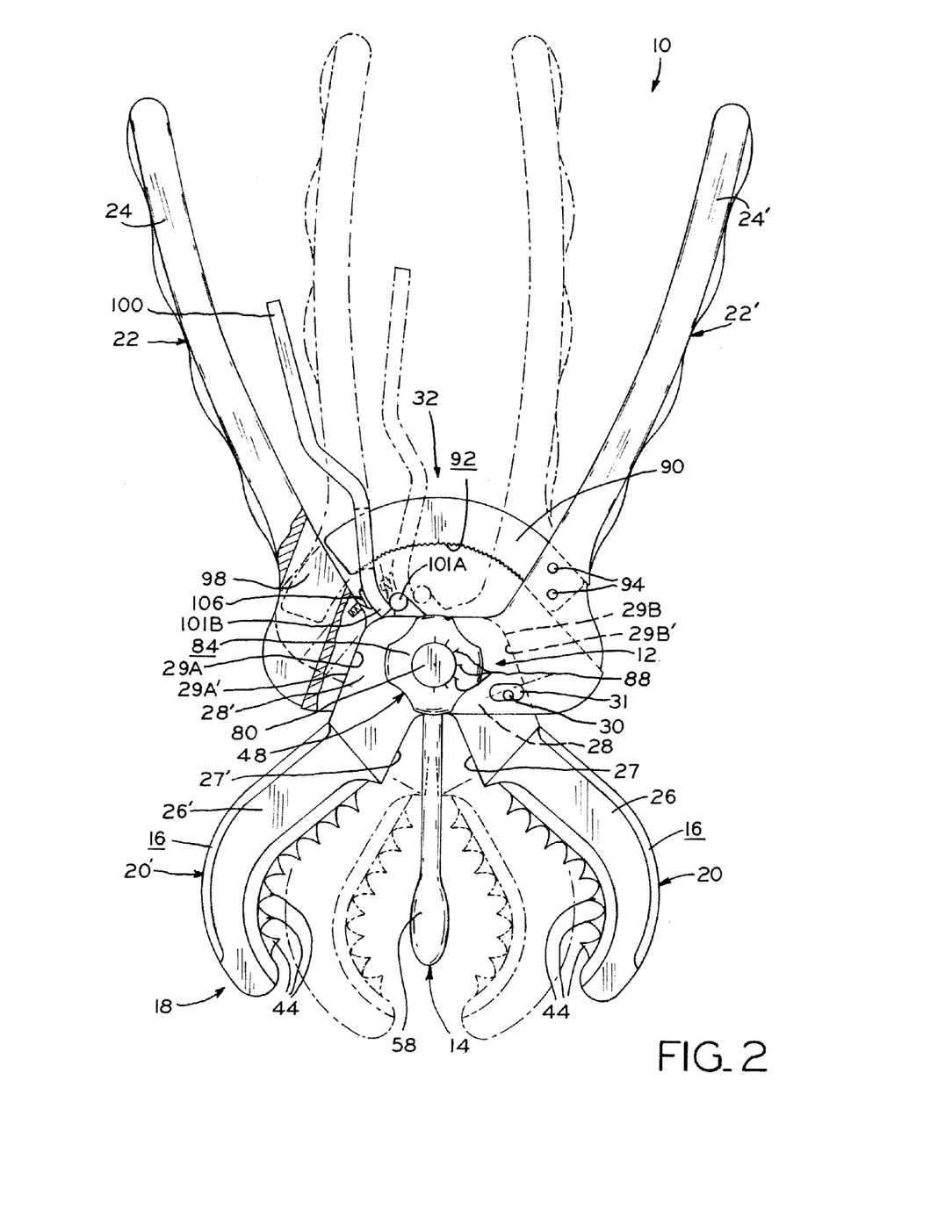
FIG. 2 is a top plan view of the patellar resection instrument shown in FIG. 1, illustrating open and closed configurations of the instrument.

Referring to FIGS. 2 and 4, one end of torsion spring 30 engages pivot 28' of instrument body 22' at aperture 31' (FIGS. 2 and 4), while the other end of torsion spring 30 engages pivot 28 of instrument body 22 at aperture 31 (FIG. 4). Thus, torsion spring 30 is acted on, and may be compressed by handles 24, 24' of instrument bodies 22, 22' respectively. The travel of instrument bodies 22, 22' toward the open position is limited by abutting contact between shoulders 29A, 29A' formed near pivots 28, 28' respectively, and by the corresponding opposite-side shoulders 29B, 29B' (FIG. 2). On the other hand, the travel of instrument bodies 22, 22' toward the closed position is limited by abutting contact between shoulders 27, 27' formed between clamp arms 26, 26' and pivots 28, 28' respectively.

Instrument bodies 22, 22' are held together at pivots 28, 28' by cooperation between threaded end 36 of adjustment body 46 (discussed below) of depth adjustment assembly 12 and bushing 38 threadably coupled thereto. On assembly, torsion spring 30 is placed between instrument bodies 22, 22' at pivots 28, 28' and threaded end 36 is passed through apertures 40, 40' formed at pivots 28, 28'. Bushing 38 is then threadably coupled to threaded end 36 to pivotably couple bodies 22, 22' to one another. In the exemplary embodiment illustrated in FIG. 4, a lower low-friction washer 42, is placed between bushing 38 and instrument body 22, and an upper low-friction washer 42' is placed between depth adjustment assembly 12 and instrument body 22' to facilitate smooth rotatable motion of instrument bodies 22, 22' with respect to one another, and to facilitate smooth rotatable motion between depth adjustment assembly 12 and instrument body 22'. Low friction washers 42, 42' may be coated with Teflon® material (Teflon® is a registered trademark of E. I. du Pont de Nemours and Company Corporation of Wilmington, Del.), for example.

Clamp arms 26, 26' each include jaws 44 extending inwardly therefrom for firmly grasping patella P as described in detail below. Cut slots 20, 20' are formed in clamp arms 26, 26', respectively above jaws 44, such that jaws 44 will remain engaged with patella P after the resection of same is complete. The lower surfaces of cut slots 20, 20' are substantially coplanar when patella resection instrument 10 is assembled, thereby forming coplanar lower cut guide surfaces 16. After the resection procedure is complete, lower cut guide surfaces 16 are also coplanar with the remainder of patella P. As a result of this coplanarity, lower cut guide surfaces 16 provide data for establishing the total resection depth D of patella P, as described in detail below.

Figure 5:
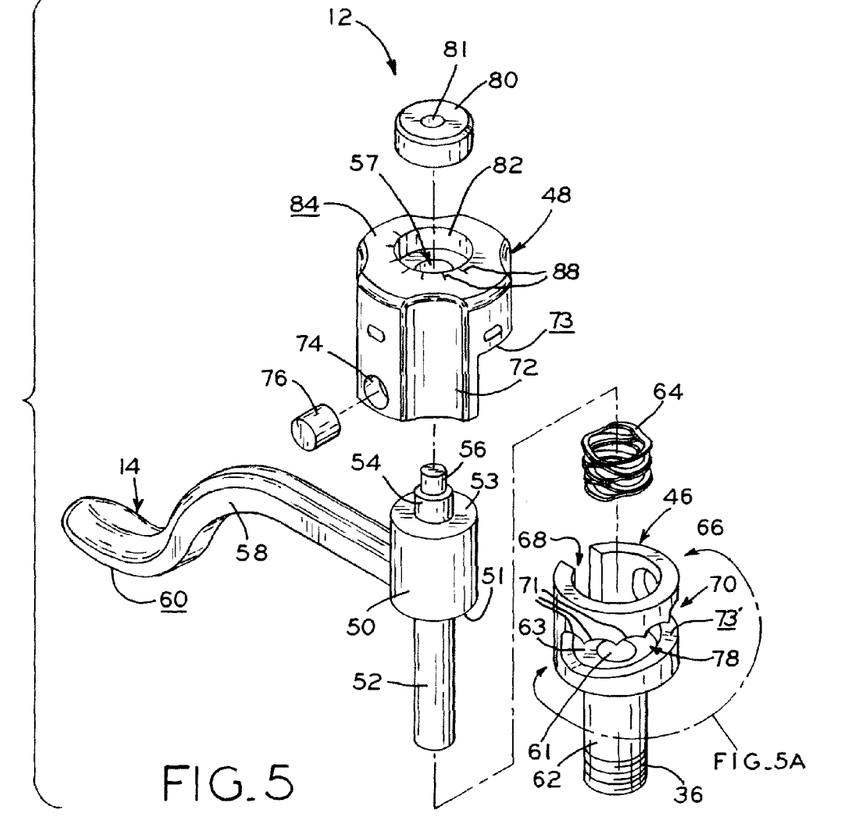
FIG. 5 is an exploded, perspective view of a depth adjustment assembly in accordance with the present disclosure.

Turning now to FIG. 5, depth adjustment assembly 12 includes resection depth stylus 14, adjustment body 46, and adjustment knob 48. Stylus 14 includes pivot body 50, pin 52, knob mounting shaft 54, cap mounting shaft 56, and stylus extension 58. Stylus extension 58 includes bone contacting surface 60 along a lower end thereof. Pin 52 is received within longitudinal aperture 61 formed in lower shaft 62 of adjustment body 46, with spring 64 disposed between shoulder 63 atop shaft 62 and lower shoulder 51 of pivot body 50. Spring 64 biases stylus 14 upwardly away from adjustment body 46 to facilitate discrete adjustment of assembly 12, as discussed in detail below. Pivot body 50 and spring 64 are received within head portion 66 of adjustment body 46. In order to accommodate stylus extension 58, head portion 66 includes slot 68. Head portion 66 of adjustment body 46 further includes scalloped region 70, which forms the basis for the discrete adjustment of stylus 14 to select resection depth D, as described in detail below.

With pivot body 50 received in head portion 66 of adjustment body 46, knob mounting shaft 54 is positioned within aperture 57 formed through knob 48. Similarly, cap mounting shaft 56 may be received within aperture 81 formed through knob cap 80 once knob cap 80 is positioned within counterbore 82 formed in knob 48 (discussed further below). The close fit between shafts 54, 56 and apertures 57, 81, respectively, centers knob 48 upon pivot body 50 of stylus 14. Thus, knob 48 remains axially aligned on stylus 48 as knob 48 is rotated to adjust resection depth D. As discussed below, knob 48 and stylus 14 move upwardly and downwardly together as resection depth D is adjusted, such that shafts 54, 56 remain in contact with apertures 57, 81 respectively through the range of adjustment for depth adjustment assembly 12.

Figure 5A:
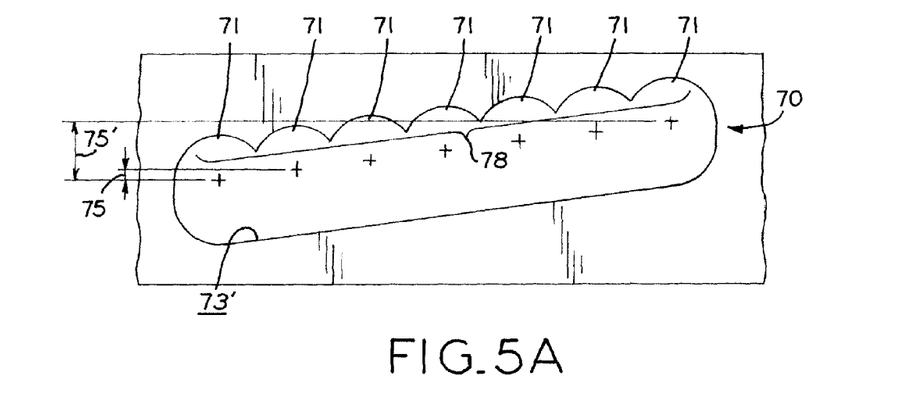
FIG. 5A is a side, elevation, detail view of a scalloped region of the depth adjustment assembly shown in FIG. 5, in which the rounded profile of the scalloped region is shown as it would appear if unfolded into a planar configuration.

Knob 48 includes skirt 72 having aperture 74 sized to receive pin 76. When knob 48 is mounted to knob mounting shaft 54 of stylus 14, skirt 72 partially covers head portion 66 of adjustment body 46, thereby allowing pin 76 to engage scalloped region 70. On assembly, knob 48 is held down against the biasing force of spring 64 to align aperture 74 in skirt 72 with scalloped region 70. Pin 76 is then pushed through aperture 74 and into scalloped region 70 (see, for example, FIG. 3B). Pin 76 can be interference-fit through aperture 74 or welded in place, for example. When knob 48 is subsequently released, spring 64 urges pin 76 into the nearest adjacent trough 71 (FIG. 5A) formed in scallops 78. More specifically, pin 76 is acted upon by spring 64 (via pivot body 50), which pushes upwardly on knob 48. This spring-biased interaction between knob 48 and scalloped region 70 of adjustment body 46 forms the basis for discrete adjustment of patella resection depth D, and also provides tactile feedback indicative of such adjustment (as described below).

Referring still to FIG. 5, knob cap 80 is received within counterbore 82 formed in top surface 84 of knob 48. On assembly, knob cap 80 is fixed to cap mounting shaft 56 of stylus 14 (such as by welding), and rotatably received within counterbore 82 of knob 48, so that knob 48 is rotatable with respect to stylus 14 and adjustment body 46, but is only axially moveable to the extent permitted by cooperation of pin 76 with scalloped region 70 (as described below). More particularly, upper shoulder 53 receives a corresponding surface within knob 48 (not shown), which are biased into abutting engagement by spring 64 when knob 48 is assembled to stylus 14 as discussed below.

Figure 3:
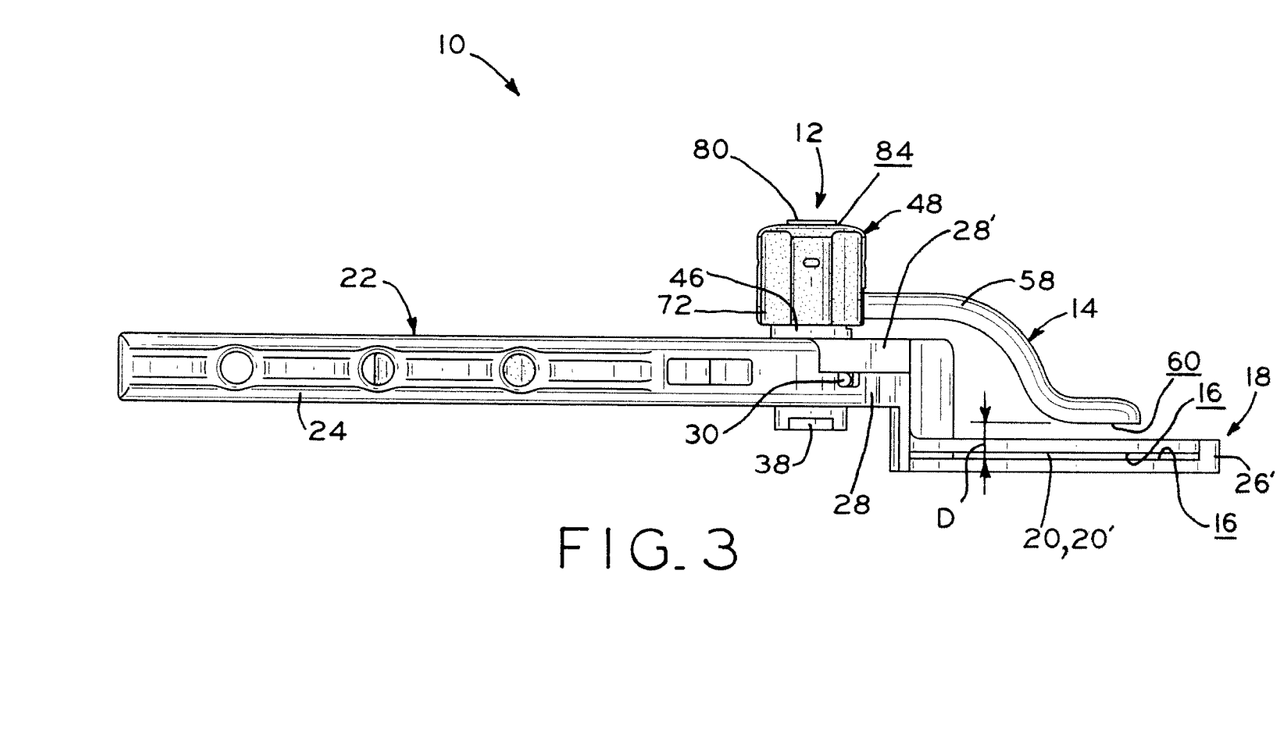
FIG. 3 is a side, elevation view of the patellar resection instrument shown in FIG. 1.

In an exemplary embodiment, top surface 84 of knob 48 includes resection depth markings 88 indicative of resection depth D (FIG. 3). Markings 88 are spaced on knob 48 to correspond to the rotational orientation of knob associated with each of troughs 71, such that each discrete position of stylus 14 is represented by an individual mark. Markings are indexed to a reference mark, which may be formed on stylus extension 58 of stylus 14, or knob cap 80, for example. After assembly of instrument 10, any discrepancy between the distance measured between lower cut guide surfaces 16 and bone contacting surface 60 of stylus 14 and the intended resection depth D (indicated by the numerical values of markings 88) can be corrected by machining away material from bone contacting surface 60 until the distance exactly matches the numerical values of resection depth markings 88. When the exact match is found, this distance is equal to resection depth D. In an exemplary embodiment, extra material is provided on stylus extension 58 at bone contacting surface 60 to ensure sufficient material is present for removal by the above-described calibration process.

Figure 2A:
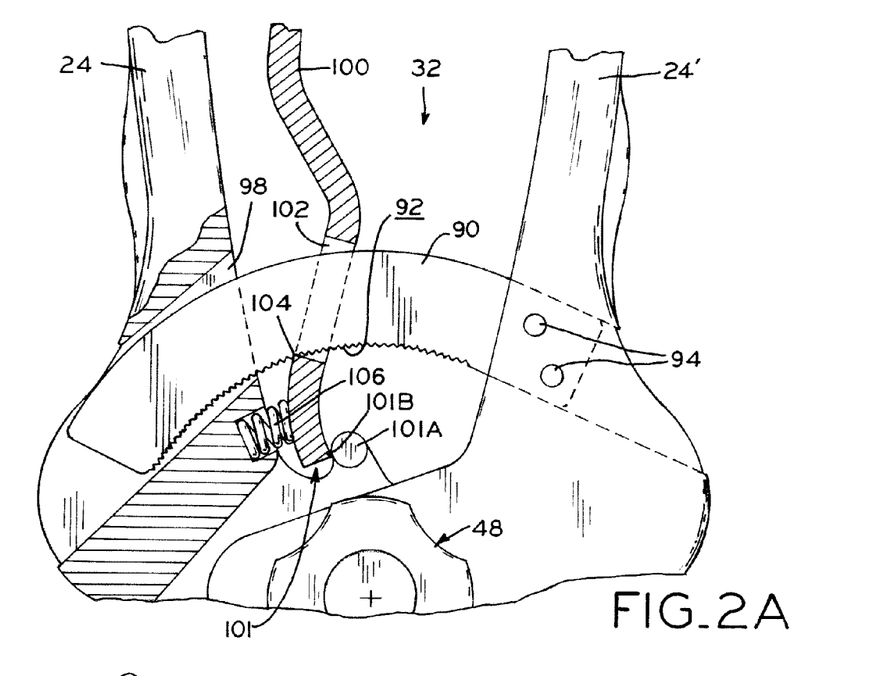
FIG. 2A is a partial, top plan view of the patellar resection instrument shown in FIG. 2, illustrating an engaged ratchet mechanism.
Figure 2B:
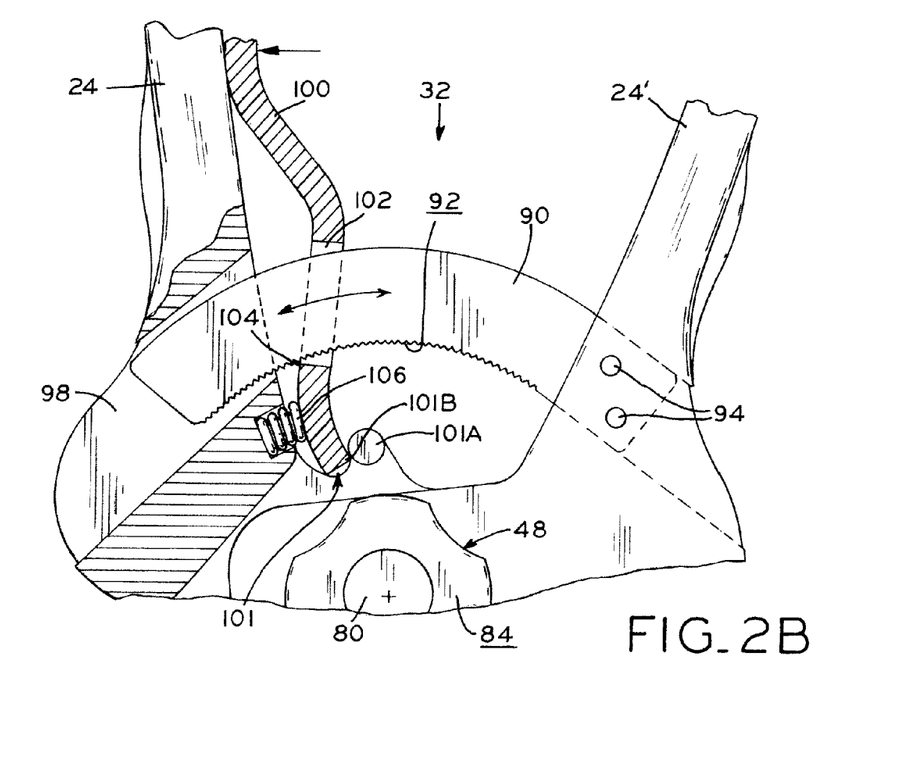
FIG. 2B is a partial, top plan view of the patellar resection instrument shown in FIG. 2, illustrating a disengaged ratchet mechanism.

As best seen in FIGS. 2, 2A, 2B and 4, patella resection instrument 10 further includes ratchet mechanism 32 for holding clamping portion 18 in a closed configuration (shown in dashed lines in FIG. 2). Referring to FIG. 4, ratchet mechanism 32 includes arcuate rack 90 having toothed concave surface 92 formed thereon. Arcuate rack 90 is fixed to handle 24' at one end, such as by pins 94 passing through apertures 96 formed through handle 24' and arcuate rack 90, with the other end of rack 90 free. As patella resection instrument 10 is actuated between opened and closed positions (FIG. 2), the free end of arcuate rack 90 extends into slot 98 formed in handle 24. Release lever 100 is pivotably connected to handle 24 at ratchet pivot 101 (FIG. 2), and includes release lever slot 102 (FIG. 4) through which the free end of arcuate rack 90 passes on its way into slot 98. Referring to FIGS. 2A and 2B, ratchet pivot 101 is formed by the abutting contact of pivot pin 101A with release lever pivot end 101B, with such contact maintained by the biasing force of spring 106. Release lever 100 is captured to instrument bodies 22, 22' by arcuate rack 90, which is surrounded on all sides by release lever slot 102. In alternative embodiments, release lever 100 may be hingedly connected to one of instrument bodies 22, 22' or otherwise connected in any suitable manner.

As best seen in FIGS. 2A and 2B, release lever slot 102 includes pawl 104, which is located and shaped to selectively engage toothed concave surface 92 as arcuate rack 90 passes through release lever slot 102. More particularly, pawl 104 is releasably engaged with toothed surface 92 when lever 100 is spaced from handle 24 (FIG. 2A), and becomes disengaged when lever 100 is pulled toward handle 24 (FIG. 2B). To maintain ratchet mechanism 32 in a "normally engaged" configuration, spring 106 biases release lever 100 away from handle 24. The teeth formed on toothed concave surface 92 cooperate with pawl 104 to allow surface 92 to pass through aperture 102 in lever 100 as instrument 10 is closed, even if lever 100 is under the biasing force of spring 106. However, the teeth on surface 92 cooperate with pawl 104 to prevent any opening movement of rack 90 back through aperture 102 when pawl 104 is engaged with surface 92, as shown in FIG. 2A. For example, the teeth of toothed surface 92 may present an angled surface to pawl 104 which can be "climbed" to allow instrument 10 to be freely manipulated from an open to a closed configuration. On the other hand, the teeth of toothed surface 92 may present a vertical or reverse-angled surface which locks pawl 104 against surface 92, thereby only allowing instrument 10 to be reconfigured from a closed to an open position if release lever 100 is actuated (against the biasing force of spring 106) to disengage pawl 102 from toothed concave surface 92 as shown in FIG. 2B.

Although ratcheting mechanism 32 is described as the mechanism for locking instrument 10 in a closed configuration, it is contemplated that other locking devices may be used in accordance with the present disclosure. Such locking mechanisms might include other ratchet mechanism configurations, cam/follower systems, and physical stops such as cotter pins and fasteners.

In use, patella resection instrument 10 can be set to a particular resection depth D for removal of a known quantity of patella P. Resection depth D is first set to a desired level by manipulation of depth adjustment assembly 12, and instrument 10 is subsequently affixed to patella P. Advantageously, the novel design of depth adjustment assembly 12 reliably maintains resection depth stylus 14 in the originally set position throughout the resection of patella P, even where vibrations, shocks or other forces are transmitted to instrument 10 during the resection process.

Figure 3A:
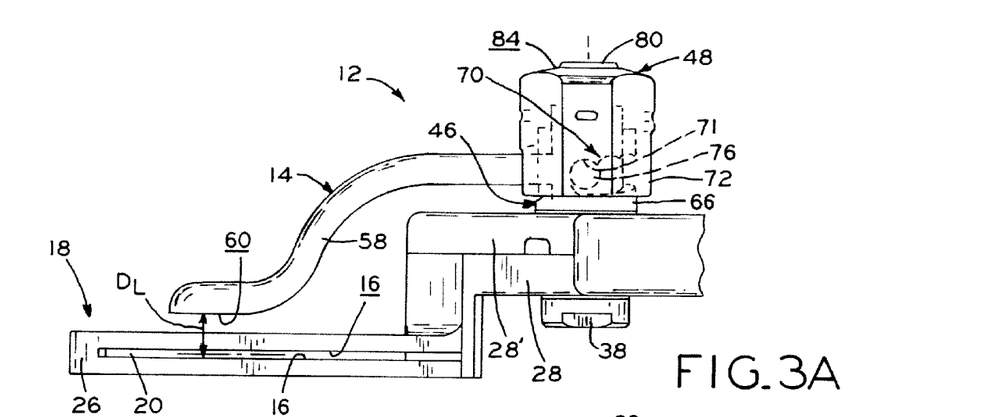
FIG. 3A is a partial side, elevation view of the patellar resection instrument shown in FIG. 3, illustrating the depth adjustment assembly in a lowered configuration.

Prior to attachment of clamping portion 18 to patella P, resection depth D (FIG. 3) is set by manipulation of depth adjustment assembly 12. More particularly, resection depth D is set by rotating knob 48 to engage knob pin 76 within a selected one of troughs 71 among scallops 78. For example, referring to FIG. 3C, stylus 14 may be placed in a raised configuration to define resection depth $D_R$, such that a relatively large amount of patella P would be resected. In this raised configuration, pin 76 engages the uppermost trough 71 in scalloped region 70. As shown in FIGS. 3A-3C, scalloped region 70 includes a plurality of troughs 71, with each successive trough at a different position relative to other adjacent troughs 71. In the illustrated embodiment, troughs 71 successively index upwardly from a lowest position (FIG. 3A) to a highest position (FIG. 3C), with each intermediate position slightly higher than the previous one. In an exemplary embodiment illustrated in FIG. 5A, each position indexes downwardly by a trough-to-trough distance 75 of approximately 0.50 mm (0.0197 in). Scalloped region 70 includes seven troughs 71, yielding a net adjustability 75' (FIG. 5A) of resection depth stylus 14 of about 3.0 mm (0.1181 in). However, it is contemplated that any level of total adjustment with any number of intermediate indexed positions may be chosen as required or desired for a particular application.

Figure 3B:
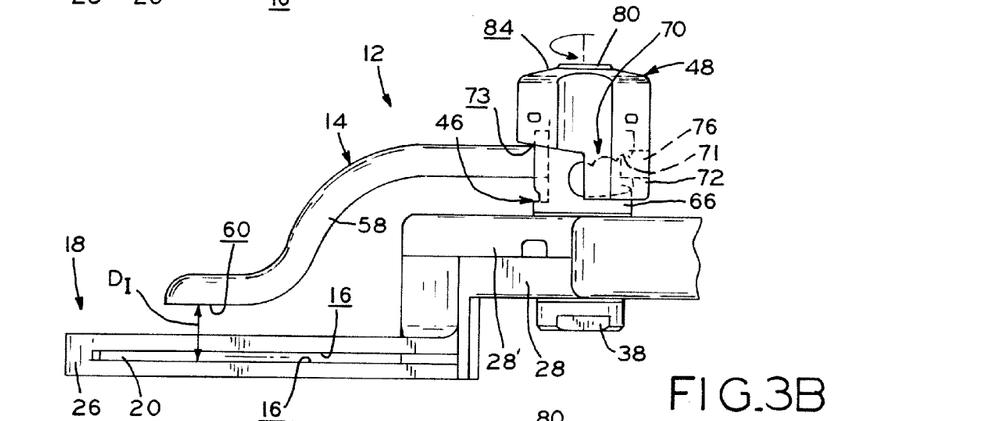
FIG. 3B is a partial side, elevation view of the patellar resection instrument shown in FIG. 3, illustrating the depth adjustment assembly in an intermediate configuration.
Figure 3C:
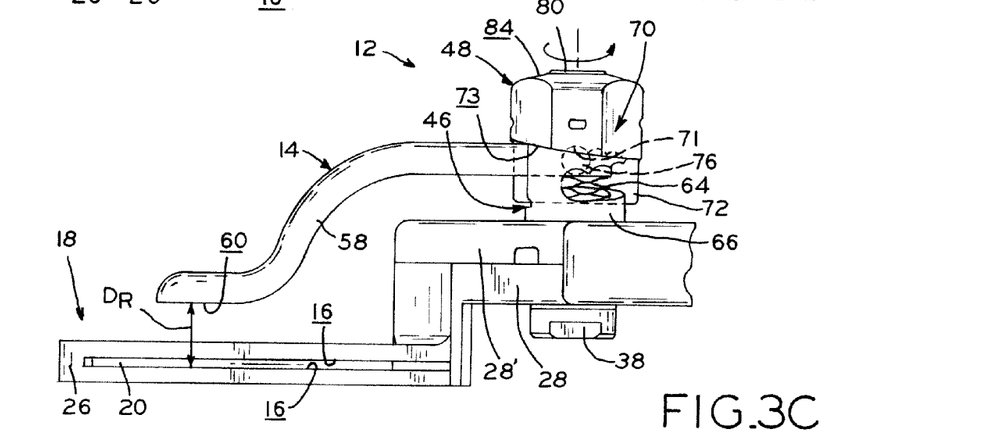
FIG. 3C is a partial side, elevation view of the patellar resection instrument shown in FIG. 3, illustrating the depth adjustment assembly in a raised configuration.

Referring to FIG. 3B, depth adjustment assembly 12 is shown in an intermediate configuration yielding resection depth $D_I$ between bone contacting surface 60 of stylus 14 and lower cut guide surfaces 16 of clamping portion 18. To adjust depth adjustment assembly 12 from the raised configuration shown in FIG. 3C to the intermediate configuration shown in 3B, knob 48 is pressed downwardly against the biasing force of spring 64 to dislodge knob pin 76 from the uppermost trough 71 (FIG. 3C). Knob 48 is then rotated, with pin 76 riding smoothly along ramped surface 73' of scalloped region 70 until markings 88 indicate a desired resection depth, such as intermediate resection depth $D_I$. Adjustment knob 48 is then released. In the absence of any user manipulation or other force external to depth adjustment assembly 12, spring 64 biases pin 76 into the nearest trough 71 of scallops 78. Alternatively, knob 48 can simply be rotated, causing pin 76 to follow the surface of scallops 78 to "click" into position at each of troughs 71 once the external force, i.e., the rotation of knob 48, is removed. Put another way, the absence of external manipulation forces on depth adjustment assembly 12 (i.e., via knob 48) renders all forces acting on spring 64 internal to depth adjustment assembly 12 (i.e., the counterbalancing forces from shoulders 51, 63 of pivot body 50 and lower shaft 62 respectively). When only these internal forces act on spring 64, spring 64 will bias pin 76 into the nearest adjacent trough 71, thereby placing stylus 14 in one of the discrete adjustment positions defined by scalloped region 70.

As a result of the relatively lower position of trough 71 in this intermediate position, resection depth stylus 14 has moved downwardly from the position shown in FIG. 3C and pivot body 50 has pushed further into head portion 66 of adjustment body 46 against the biasing force of spring 64. More particularly, the abutting engagement between an inner surface of knob 48 (not shown) and upper shoulder 53 of pivot body 50 causes any downward movement of knob 48 to be transferred to stylus 14. As the position of knob 48 is lowered or raised by engaging pin 76 with a lower or higher trough 71, the spring-biased abutting engagement between knob 48 and pivot body 50 ensures that stylus 14 will also lower or raise correspondingly. Alternatively, ramped surface 73 formed on knob 48 (FIGS. 3B and 3C) may contact stylus extension 58 directly to urge stylus 14 downwardly as pin 76 of knob 48 is moved into engagement with troughs 71 having different heights. In this case, a space is formed between upper shoulder 53 of pivot body 50 and the adjacent surface within knob 48.

Referring to FIG. 3A, depth adjustment assembly 12 may be similarly reconfigured into a fully lowered configuration to define resection depth $D_L$ between bone contacting surface 60 of stylus 14 and lower cut guide surfaces 16 of clamping portion 18. In the lowered configuration of FIG. 3A, pin 76 is received by the lowermost trough 71 of scallops 78, such that knob 48 urges stylus 14 into its lowest position via contact with upper shoulder 53 of pivot body 50. Pivot body 50 is also more fully received within head portion 66 of adjustment body 46, such that spring 64 is in a fully or nearly fully compressed state. Depth adjustment assembly 12 may, in the exemplary embodiment shown, be reconfigured into any of the seven discrete positions defined by troughs 71 in a similar manner.

Once the surgeon has selected a desired depth of resection D for patella P, clamping portion 18 of instrument 10 may be affixed to patella P to prepare for the resection procedure. Patella P is first exposed using conventional retraction procedures and/or other surgical methods. Patella P is typically everted, i.e., rotated away from femur F and tibia T to expose the articular surface to be resected, as shown in FIG. 1. With clamping portion 18 in an open configuration (solid lines of FIG. 2), bone contacting surface 60 of resection depth stylus 14 is placed onto the exposed articular surface of patella P.

Patella resection instrument 10 is then aligned so that lower cut guide surfaces 16 are oriented with respect to patella P, as desired by the surgeon. While maintaining contact between bone contacting surface 60 and patella P, handles 24, 24' are squeezed together to bring clamping portion 18 into a closed configuration (dashed lines of FIG. 2). In order to maintain contact with the desired "high point" of patella P during this clamping procedure, depth adjustment assembly 12 may pivot with respect to pivots 28, 28' of instrument bodies 22, 22' respectively. Such pivoting is made possible because lower shaft 62 of adjustment body 46 is not rotatably fixed within apertures 40, 40' (FIG. 4). Additionally, as noted above, low-friction washers 42, 42' facilitate smooth rotation of depth adjustment assembly 12 with respect to bodies 22, 22'.

Upon contact with patella P, jaws 44 rigidly fix clamping portion 18 (and therefore, instrument 10) to patella P. As noted above, ratchet mechanism 32 allows handles 24, 24' to be freely squeezed together into the closed configuration against the biasing force of torsion spring 30, but prevents clamping portion 18 from reverting back to the open configuration under such biasing force. Thus, clamping portion 18 is maintained in the fixedly coupled state with patella P until release lever 100 is actuated at the end of the resection procedure.

With clamping portion 18 now firmly engaging jaws 44 about the periphery of patella P, and resection depth stylus 14 in contact with patella P and set to resection depth D, blade B (or any suitable cutting instrument) is passed into one of cut slots 20, 20', with one of lower cut guide surfaces 16 used to maintain blade B at the appropriate resection height. Once blade B has passed through the other of cut slots 20, 20' and is in contact with both lower cut guide surfaces 16 at both of clamp arms 26, 26', blade B may be moved throughout cut slots 20, 20' to complete the resection of patella P and fully dislodge the removed portion of patella P from the newly resected surface on the remainder of patella P.

Because resection depth D is defined by lower cut guide surfaces 16 of cut slots 20, 20', and the removed portion of patella P is the "upper" portion thereof in the context of instrument 10, lower cut guide surfaces 16 are coplanar with the resected surface of the remainder of patella P after the resection operation is complete. Thus, the thickness of blade B does not affect resection depth D, which is the distance between bone contacting surface 60 of stylus 14 and lower cut guide surfaces 16, and is equal to the total amount of bone removed from patella P. Put another way, resection depth D may be said to be the total distance from lower cut guide surfaces 16 to bone contacting surface 60, when measured along a line normal to the planar lower cut guide surfaces 16.

With the resection of patella P now complete, release lever 100 is actuated against the biasing force of spring 106 to release pawl 104 from rack 92. When so released, the biasing force of torsion spring 30 is allowed to move clamp arms 26, 26' away from one another, reconfiguring clamping portion 18 to an open configuration. The newly resected surface of patella P may then be used to implant a prosthetic patellar component in accordance with conventional methods.

Alternatively, instrument 10 may remain engaged with patella P to facilitate holding patella P during implantation of the prosthetic patellar component. To allow unfettered exposure of the resected surface, stylus 14 may be swiveled to either side by pivoting depth adjustment assembly 12 with respect to pivots 28, 28' of bodies 22, 22' respectively in the same manner as the pivoting of stylus 14 during the clamping of clamping portion 18 upon patella P (described above).

Advantageously, depth adjustment assembly 12 of instrument 10 defines a plurality of discrete depth adjustment values corresponding to known resection depths, such that resection depth D can be set to a particular value by simply manipulating knob 48 until markings 88 on top surface 84 thereof indicate that resection depth D has been set. This method of setting resection depth D is efficient and intuitive, such that a surgeon may quickly and efficiently adjust resection depth D intra-operatively. Moreover, depth adjustment assembly 12 is integral to instrument 10, in that assembly 12 remains rotatably attached to instrument bodies 22, 22' throughout the use of instrument 10. Depth adjustment assembly 12 is also integral to instrument 10, in that no parts of depth adjustment assembly 12 are separable from the remainder of instrument 10 (i.e., instrument bodies 22, 22') during use. Depth adjustment assembly 12 being integral to instrument 10 provides ease of use, storage and transport, prevents assembly 12 from coming loose from instrument 10 during the surgical procedure, and ensures that depth adjustment assembly 12 is always together with the rest of instrument 10.

Also advantageously, depth adjustment assembly 12 of instrument 10 may provide tactile and audible feedback to indicate movement between discrete depth adjustment values, in contrast to a "continuously adjustable" (i.e., threadably adjusted) system lacking predefined distances defining discrete patella resection depths. If a surgeon wishes to adjust a continuously adjustable system to a particular resection depth, the resection depth adjuster is carefully and precisely rotated to the position corresponding to the desired depth of resection. Thus, changing the resection depth a very small amount involves a very small movement of the depth adjuster in a continuously adjustable system. On the other hand, depth adjustment assembly 12 allows for the desired resection depth D to be predefined (i.e., by the locations of troughs 71 formed in adjustment body 46, as discussed above). Rather than carefully and precisely manipulating assembly 12 with small movements of knob 48, the surgeon can simply adjust knob 48 into one of the discrete, predefined resection depth positions with a quick, relatively large movement. The precision of the final resection depth D comes from the automatic movement adjustment assembly 12 into the desired position, rather than from manual fine-tuning.

More particularly, knob pin 76 (FIG. 5) may ride over scallops 78 of scalloped region 70 as knob 48 is rotated, such that pin 76 "snaps" into respective troughs 71 of scallops 78. With each such "snap," a surgeon using instrument 10 can both feel and hear knob 48 engaging a new discrete, predefined resection depth position under the force provided by spring 64. Thus, depth adjustment assembly 12 eliminates ambiguity as to whether stylus 14 is in a particular discrete position, because spring 64 will bias pin 76 fully into one of recesses 71 in scalloped region 70. Because there are a finite number of recesses 71, such as seven recesses in the exemplary embodiment disclosed herein, simply releasing knob 48 ensures that resection depth stylus is in one of the discrete predefined positions.

A further advantage of instrument 10 is that vibrations and other forces transmitted throughout the components of instrument 10 during a resection procedure will not cause depth adjustment assembly 12 to loosen, nor will resection depth stylus 14 change position absent manipulation of knob 48. Spring 64 biases pin 76 firmly into a respective one of troughs 71, and troughs 71 are sufficiently deep to ensure that vibrations and other forces transmitted to depth adjustment assembly 12 during normal usage of instrument 10 will result in pin 76 becoming dislodged from the chosen trough 71 corresponding to a desired resection depth D. Moreover, a surgeon can view resection depth markings 88 at any time during use of instrument 10 to visually verify that stylus 14 remains in the chosen position.

While this invention has been described as having an exemplary design, the present disclosure can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the scope of the appended claims.

What is claimed is:

1. A surgical instrument for use in resection of a patella, the instrument comprising:
   first and second instrument bodies pivotally connected to one another at a junction between a handle and a clamp arm of each of said first and second instrument bodies, wherein said clamp arm of one of said first and second instrument bodies comprises a cut guide defining a cut guide surface; and
   an integral depth adjustment assembly disposed completely on a first side of said cut guide, the integral depth adjustment assembly comprising:
      a stylus slidably coupled to an adjustment body, said stylus having a bone contacting surface movable between a plurality of discrete stylus positions, each of said plurality of discrete stylus positions defining a predefined stylus distance between said cut guide surface and said bone contacting surface;
      the adjustment body comprising a scalloped region having a plurality of troughs defining said plurality of discrete stylus positions;
      a knob coupled to and configured to move said stylus between said plurality of discrete stylus positions by successively engaging each of said plurality of troughs of said scalloped region; and a biasing element biasing said knob into engagement with one of said plurality of troughs when said biasing element is acted upon only by forces within said depth adjustment assembly,
wherein said knob includes indexing marks indicative of said plurality of predefined stylus distances.

2. The surgical instrument of claim 1, wherein said knob comprises a pin positioned for said engagement with said one of said plurality of troughs, and said biasing element comprises a spring disposed between said stylus and said adjustment body, said spring biasing said pin toward said troughs.

3. The surgical instrument of claim 2, wherein said spring biases said knob away from said cut guide surface.

4. The surgical instrument of claim 2, wherein said first instrument body comprises a first pivot region disposed at the junction between said handle and said clamp arm of said first instrument body, and wherein said second instrument body comprises a second pivot region disposed at the junction between said handle and said clamp arm of said second instrument body, said first pivot region of said first instrument body pivotally connected to said second pivot region of said second instrument body.

5. The surgical instrument of claim 4, further comprising a ratchet mechanism including:
a rack coupled to one of said first and second instrument bodies, said rack having a toothed surface;
a release lever coupled to the other of said first and second instrument bodies, said release lever having a pawl positioned to releasably engage said toothed surface;
a second biasing element urging said pawl into engagement with said toothed surface of said rack, whereby the ratchet mechanism is operable to releasably lock said first and second instrument bodies in a closed configuration.

6. The surgical instrument of claim 1, wherein said cut guide surface is substantially planar, each of said plurality of predefined stylus distances defined as a distance from said cut guide surface to said bone contacting surface of said stylus along a line normal to said cut guide surface.

7. A surgical instrument for use in resection of a patella, the instrument comprising:
an instrument body, wherein said instrument body comprises a pair of handles and a pair of clamp arms joined at a pivot, wherein said pair of clamp arms is configured for fixing the patella to said instrument body, and wherein one clamp arm of said pair of clamp arms comprises a cut guide having a cut guide surface; and
resection depth selection means for selecting a predefined resection depth, said depth selection means disposed completely on a first side of said cut guide, coupled to said instrument body, and comprising:
a stylus having a bone contacting surface;
a scalloped region having a plurality of troughs defining different positions of said stylus;
a knob coupled to and configured to move said stylus to the different positions by successively engaging each of said plurality of troughs of said scalloped region; and
a biasing element biasing said knob into engagement with one of said plurality of troughs, wherein said predefined resection depth is equal to a distance between said bone contacting surface and said cut guide surface, and
wherein said knob includes indexing marks indicative of the different positions of said stylus distances.

8. The surgical instrument of claim 7, further comprising means for releasably locking said pair of clamp arms in a closed configuration.

9. The surgical instrument of claim 8, wherein said means for releasably locking said pair of clamp arms comprises a ratchet mechanism at least partially disposed between said pair of handles.

10. A method of resecting a patella with a surgical instrument, the instrument comprising an instrument body, wherein said instrument body comprises a pair of handles and a pair of clamp arms joined at a pivot, wherein said pair of clamp arms is configured for fixing the patella to said instrument body and wherein one clamp arm of said pair of clamp arms comprises a cut guide having a cut guide surface, and an integral depth adjustment assembly disposed completely on a first side of said cut guide, the integral depth adjustment assembly comprising:
an adjustment body;
a stylus slidably coupled to the adjustment body, the stylus having a bone contacting surface movable between a plurality of discrete positions with respect to the adjustment body, each of the plurality of discrete positions corresponding to a resection depth of the patella and defining a predefined distance between the cut guide surface and the bone contacting surface, the adjustment body comprising a scalloped region having a plurality of troughs defining the plurality of discrete positions;
a knob coupled to and configured to move the stylus between the plurality of discrete positions by successively engaging each of the plurality of troughs of the scalloped region, the knob including indexing marks indicative of the plurality of discrete positions; and
a biasing element biasing the stylus into each of the plurality of discrete positions, the biasing element biasing the knob into engagement with one of the plurality of troughs when the biasing element is acted upon only by forces within the integral depth adjustment assembly, the method comprising:
adjusting the integral depth adjustment assembly into one of the plurality of discrete positions to define the resection depth of the patella;
contacting the patella with the stylus;
while maintaining the contact between the patella and the stylus and after said step of adjusting the integral depth adjustment assembly, coupling the cut guide of the surgical instrument onto the patella; and
resecting the patella using the cut guide.

11. The method of claim 10, wherein said step of coupling the cut guide of the surgical instrument onto the patella comprises:
squeezing the pair of handles to place the pair of clamp arms in a closed configuration, so that the pair of clamp arms is attached to the patella; and
locking the pair of clamp arms onto the patella using a locking mechanism operable to releasably lock the pair of clamp arms in the closed configuration.

12. The method of claim 11, wherein said step of locking the pair of clamp arms onto the patella comprises using a ratcheting mechanism, the ratcheting mechanism including:
a rack coupled to one of the pair of handles, the rack having a toothed surface;
a release lever coupled to the other of the pair of handles, the release lever having a pawl positioned to engage the toothed surface; and
a second biasing element urging the pawl into releasable engagement with the toothed surface of the rack, the toothed surface cooperating with the pawl to prevent the pair of handles from moving from the closed configuration to an open configuration when the pawl is engaged with the rack.

* * * * *